United States Patent [19]
Otto

[11] Patent Number: 4,803,843
[45] Date of Patent: Feb. 14, 1989

[54] LOW PRESSURE REFRIGERANT CONTAMINANT TESTER

[75] Inventor: Nancy M. Otto, Clay, N.Y.

[73] Assignee: Carrier Corporation, Syracuse, N.Y.

[21] Appl. No.: 155,487

[22] Filed: Feb. 12, 1987

[51] Int. Cl.⁴ ............................................. F25B 47/00
[52] U.S. Cl. .......................................... 62/85; 62/127; 62/129
[58] Field of Search ................. 62/129, 125, 127, 149, 62/85, 77, 292, 298, 299; 73/61 R, 61.1 R, 29

[56] References Cited

U.S. PATENT DOCUMENTS

| | | | |
|---|---|---|---|
| 2,506,806 | 5/1950 | Metzger | 62/125 |
| 3,086,392 | 4/1963 | Ehrens | 62/127 X |
| 3,572,050 | 3/1971 | Bottum | 62/85 |
| 3,838,578 | 10/1974 | Sakasegawa et al. | 62/125 |
| 4,110,998 | 9/1978 | Owen | 62/125 |

Primary Examiner—Harry B. Tanner
Attorney, Agent, or Firm—Thomas J. Wall

[57] ABSTRACT

A low pressure refrigerant specimen is metered from a refrigeration system as a two phase mixture containing both a liquid phase and a gas phase. The mixture is sealed in an inflatable bag and the liquid phase is permitted to become a gas at atmospheric pressure whereby any contaminants in the sample are uniformly distributed throughout the sample. A small representative sample of the gas is drawn from the bag by a pump and the sample passed through a contaminant tester tube which provides a visual indication of the amount of one or more selected contaminants contained in the representative sample.

12 Claims, 2 Drawing Sheets

LOW PRESSURE REFRIGERANT CONTAMINANT TESTER

BACKGROUND OF THE INVENTION

A number of saturated fluorocarbon compounds and azeotropes are commonly used as refrigerants in various types of refrigeration systems. These refrigerants have different properties such as boiling points and vapor pressures that dictate to a great extent the refrigerant's suitability for any intended use. Refrigeration systems are generally classified as either high pressure systems or low pressure systems depending on the operational pressure of a particular unit. The refrigerants used in these systems are therefore commonly referred to as either high pressure or low pressure refrigerants depending upon the nature of the system in which they are used.

In many of these refrigeration systems, a small amount of oil is circulated with the refrigerant. Both the refrigerant and oil contained therein, however, tend to absorb and hold water to some degree. As a result any water finding its way into the system is captured within the refrigerant. The presence of excessive moisture within the system can cause ice to form within the system and corrode metal parts through the formation of strong mineral acids, adversely affecting the operation of the unit. Early detection and removal of this unwanted contaminant is necessary in order to maintain the system in efficient operating condition.

Acid is sometimes formed by the refrigerant being chemically broken down due to the system compressor overheating. Like water, those acids have a dew point close to the refrigerant and thus can be cycled through the equipment in the refrigerant flow and build up in the refrigerant to a level where the system is eventually damaged. Contaminant tester tubes have been developed that are arranged to detect the amount of acid and water in a high pressure refrigerant sample.

In high pressure systems, the presence of acids and water is detected by drawing a high pressure sample from the system through the purge valve. The refrigerant sample is typically at a pressure of about 200 psi and is thus thoroughly vaporized. The sample is passed through a flow restriction designed to meter a volume of refrigerant sample. The sample, which is still in the vapor phase is then passed through the tester tube where it reacts with specially prepared chemicals to give a visual indication of the amount of acid and water contained in the sample. Because the sample is drawn from the system in the vapor phase throughout the testing period, any contaminants in the sample are homogenously distributed within the sample. The percentage of a given contaminant in a known amount of sample is thus truly representative of the percentage of the contaminant present in the refrigerant contained within the system.

Attempts to adopt contaminant tester tube for use in testing low pressure systems have, however, heretofore been generally unsuccessful. The low pressure refrigerants generally are those that have normal boiling points at or below room temperature. Under normal operating conditions these refrigerants will exit the system in the form of wet mixture wherein part of refrigerant is in the liquid phase and part in the vapor phase. Accordingly, the distribution of contaminants within the sample is non uniform and thus not representative of the amount of contaminant found in the system. The flow pressures make the sample difficult to handle and the sample flow through the tester tube is unpredictable. A high percentage of liquid in the sample further tends to degrade the sensitivity of the detecting chemicals and thus leads to erroneous sample readings.

SUMMARY OF THE INVENTION

It is therefore an object of the present invention to obtain a representative sample of a refrigerant drawn from a low pressure refrigeration system.

It is a further object of the present invention to accurately test a low pressure refrigerant for the presence of given contaminants using a contaminant tester tube.

Another object of the present invention is to simplify the detection of contaminants entrained within a refrigerant contained in a low pressure refrigeration system.

These and other objects of the present invention are attained by metering a two phase refrigerant specimen containing contaminants from a low pressure refrigeration system into an inflatable bag. The bag is sealed against leakage and the two phase mixture allowed to equilibrate at ambient pressure to generate a homogeneous gas within the sealed bag. A pump is used to draw a representative sample of known volume from the bag and pass the sample through a contaminant tester tube, at a uniform velocity. Chemicals contained in this tester tube react with known contaminants [acid and water] to provide an indication of the percentage of contaminants contained in the refrigerant.

BRIEF DESCRIPTION OF THE DRAWING

For a better understanding of these and other objects of the present invention, reference is made to the detailed description below which is to be read in conjunction with the following drawings, wherein.

DETAILED DESCRIPTION OF THE INVENTION

Figure 1:
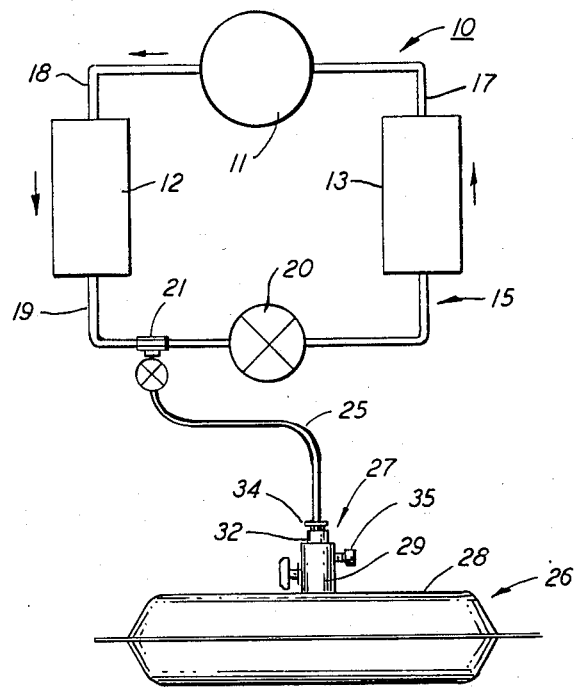
FIG. 1 is a diagrammatic view showing a refrigerant sample specimen being metered from a low pressure refrigeration system into an inflatable bag.

Referring initially to FIG. 1, there is illustrated a low pressure refrigeration system, generally referenced 10, which includes a compressor 11, a condenser 12, and an evaporator 13. The components of the system are joined by means of a suitable closed loop flow circuit 15 that includes a compressor inlet line 17, a compressor discharge line 18, and a liquid line 19 extending between the condenser and evaporator units. An expansion device 20 is operatively connected into the liquid line. A purge valve 21 of conventional design is connected into the liquid line between the expansion device and the evaporator unit which is normally used to drain refrigerant from the system and to charge new refrigerant into the system. A refrigerant specimen is shown being taken from the system through the purge valve in FIG. 1 for the purpose of testing the specimen for contaminants.

Figure 2:
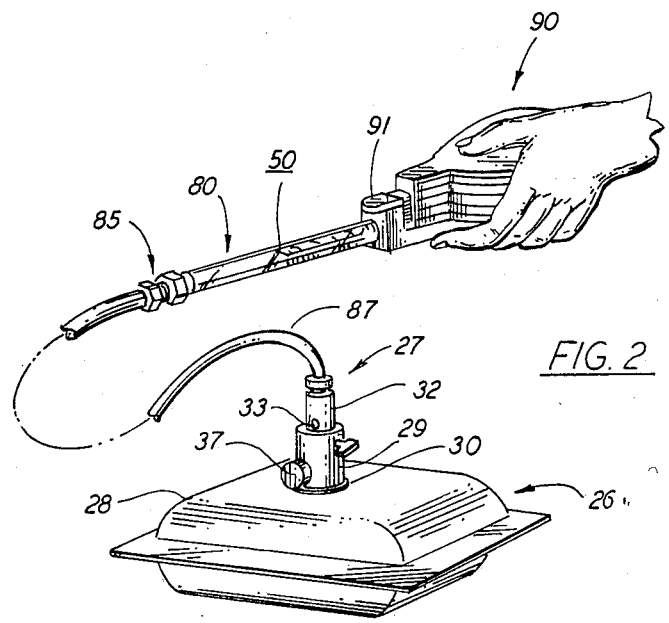
FIG. 2 is a further view showing a representative sample of the low pressure refrigerant contained within the inflatable bag being passed through a contamination tester tube.

A refrigerant specimen is taken from the purge valve and transmitted via hose 25 into an inflatable bag 26 having a one liter capacity. The bag is fabricated of a transparent material to permit the presence of a liquid contained therein to be visually perceived. A closure device 27 is mounted within the top wall 28 of the bag. The closure device contains two telescoped cylindrical members that include an outer stationary member 29 that is secured in the top wall 28 of the bag by a clamping ring 30 and an inner movable member 32 that is slidably retained within the stationary member. Internal seals not shown are mounted between the two members to provide a sliding leak proof joint therebetween. A thumb screw 35 is threaded into the side wall of the stationary member that is capable, when tightened down, to clamp the movable member at a desired position within the stationary member. The movable member contains a purge hole 33 that is exposed to atmosphere when the movable member is raised to an extended position, as shown in FIG. 2, and closed within the stationary member when the movable member is restricted, as shown in FIG. 1.

The closure device further includes a manually operated shut-off valve 37 which when closed prevents the specimen trapped in the bag from escaping. The distal end of the movable member has a threaded opening which the distal end 34 of the hose is screwed to, providing a leak tight connection.

When drawing a refrigerant specimen from the refrigeration system, the movable member of the closure device is first extended fully with purge hole open to the atmosphere so that the hose can be purged by the system's refrigerant. After approximately thirty seconds, the movable member is retracted fully inside the encompassing stationary member to prevent refrigerant from escaping through the purge hole and the shut off valve 37 and purge valve 20 are both opened allowing the two phase refrigerant mixture to be metered from the system into the inflatable bag. After about five milliliters of liquid specimen has been collected in the bag, the shut-off valve is closed sealing the specimen in the bag. The purge valve is now closed and the movable member is extended thus allowing refrigerant trapped in the hose to escape to atmosphere through the purge hole. The hose is disconnected releasing the bag from the refrigeration system.

The two phase mixture sealed in the bag is permitted to equilibrate at atmospheric temperature. Accordingly, refrigerant in the liquid phase is permitted to evaporate which results in a homogeneous gas filling the bag which contains representative amounts of contaminants uniformly distributed therein. Passing a representative sample from the bag through a tester tube will provide accurate information concerning the presence of water and/or acid in the refrigerant contained in the system.

Figure 3:
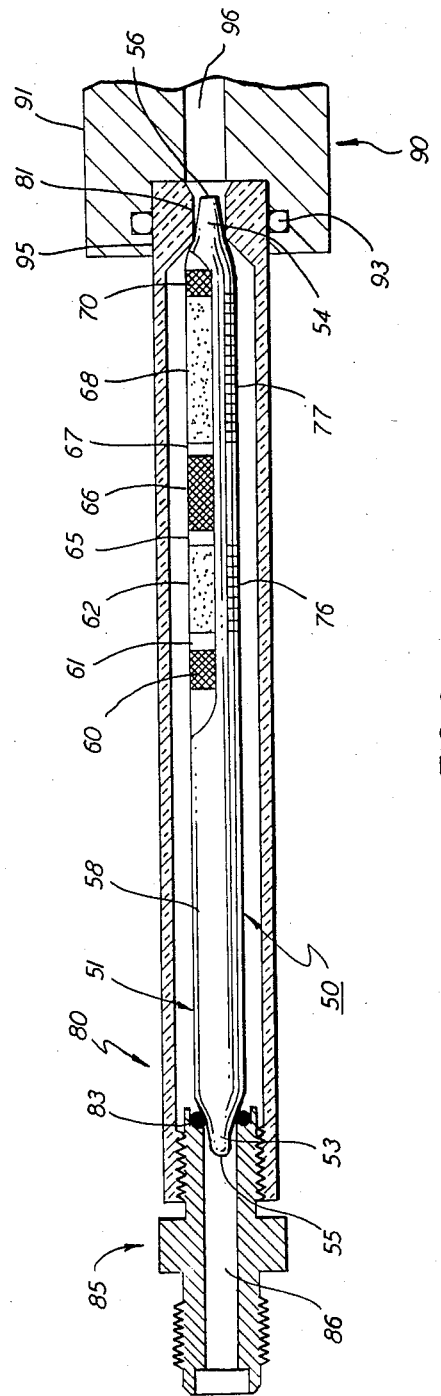
FIG. 3 is an enlarged side elevation in section showing in greater detail the construction of the contamination tester tube.

Upon the refrigerant being equilibrated within the bag, a small volume of representative sample is drawn from the bag to test for contaminants. Referring to FIG. 3, there is illustrated a disposable multiple contaminant testing tube 50 for detecting the presence of contaminants in an evaporated refrigerant. In this particular embodiment, testing tube 50 is designed to test for two particular contaminants which are acid and water. Testing tube 50 comprises a generally cylindrical tube 51 made of a transparent material, such as glass. The tube has oppositely disposed tapered ends terminating in a frangible upstream tip 53 and a similarly frangible downstream tip 54. Tips 53 and 54 are designed to be open when the tube is placed in use by breaking away the sealed ends of the tube to expose an upstream opening 55 and a downstream opening 56 which are generally conical in cross sectional form.

The testing tube is divided into a demister zone 58 for removal of oil and a contamination indicating zone 59. The demister zone extends from the upstream end 52 of the tube to about half-way along the length thereof and is essentially an open section that permits entrained oil in the representative sample to settle out previous to the remaining part of the sample reaching indicating zone 58. Starting at the upstream end of the indicating zone, the tube serially contains a length of brass screen 60 adjacent to which is a glass fiber disk 61 followed by the water removal and moisture indicating section of the tube 62. On the exit side of the moisture indicating section, a second glass fiber disk 65 is mounted along with a roll brass screen 66 and a third glass fiber disk 67. Immediately thereafter is the acid indicating section 68 of the tester tube which is followed by a length of brass screen 70.

The chemicals making up the water removal and moisture indicating section of the tube along with the acid indicating section are located in the tube relative to indicia 76 and 77, respectively. The primary function of the screens and disk members is to maintain the indicating media within the indicating sections as well as providing physical separation for the chemicals contained in the two indicating sections. The brass screens further filter out any particular material that might be entrained within the representative sample as it moves through the tube. In the present embodiment of the invention cobaltous chloride is used as a moisture indicator. The material is mixed with sand and applied to the inside wall of the tube within moisture removal section 62. When water is brought in contact with the chemical material, the material changes color from blue to pink. The acid indicating media includes a mixture of bromophenol blue, ethanol, and glycerol which is coated again upon a sand carrier coated upon the interior surface of the tube within the acid indicating section 68. When an acid is brought into contact with the bromophenol blue, its normal blue color changes to yellow. By measuring the axial length of discoloration along the indicating scales, the amount of each contaminant in the sample can be determined.

As further illustrated in FIG. 3, the contamination tester tube is contained within a housing 80 that is made of a generally transparent material such as plexiglass. The downstream end 54 of the tube is mounted within a conical seat 81. The opposite or upstream end of the tube 53 is seated in an O-ring 83 that is contained in a threaded coupling 85. The coupling is threaded into the upstream end of the housing as shown. The connector has a hole 86 passing therethrough which communicates in assembly with the tube opening 55 to permit refrigerant gas to pass freely into the tube.

As best illustrated in FIG. 2, the coupling is adapted to be threaded onto one end of a sampling line 87 while the other end of the line is adapted to be threaded onto the movable member 32 of the bag closure device 27. a hand operated bellows pump 90 is used to draw a sample of refrigerant gas from the bag and through the tester tube. The pump has a union 91 that is adapted to receive the downstream end of the tester tube housing therein. As shown in FIG. 3 an O-ring seal 93 is contained within the entrance 95 of the union to provide a gas tight joint between the tester tube housing and the union. When the housing is seated in the entrance 95, the suction port 96 of the pump is placed in communication with the downstream opening 56 of the tester tube. The pump is designed to draw approximately one hundred cubic centimeters of sample through the tester tube for each stroke of the pump.

A hand operated bellows pump 95 is used to draw a small volume of representative gas sample from the bag after the liquid has completely evaporated. The pump as illustrated in FIGS. 2 and 3, is attached to the downstream end of the tester tube container. The connector mounted on the upstream end of the container is coupled to a length of tubing 96 which, in turn, is connected to the closure device of the inflatable bag in the same manner as described with reference to the sampling tube. The pump is arranged to draw approximately one hundred cubic centimeters of representative sample through the tester tube each time that the pump is manually stroked.

To draw a representative sample from the bag, the movable cylindrical member of the closure device is again retracted within the stationary member thereby shutting off the drain hole. The shut-off valve is then opened and the pump is stroked to draw a given amount of sample gas through the tester tube. If any water is present in the gas sample, it will be absorbed by the cobaltous chloride in the water indicating section 62 turning this chemical from its normal blue color to pink. The amount of water vapor present in the sample is measured by the axial length of discoloration along the indicating scales 76. After the sample has been tested for water, it is passed through the acid testing section 68 of the tube where the sample is exposed to bromophenol blue. The presence of any acid in the sample causes this chemical to change from its normal blue color to yellow. Here again, the length of discoloration along the axis of the indicating section provides an indication of the amount of acid present in the sample.

The finding of excessive amounts of water and acid in the refrigerant is the basis for replacing the refrigerant within the refrigeration system or, alternatively, determining the cause of this type of failure.

While this invention has been explained with reference to the embodiment disclosed herein, it is not confined to the details set forth and this application is intended to cover any modifications and changes as may come within the scope of the following claims.

What is claimed is:

1. A method of testing a low pressure refrigerant for contamination that includes the steps of
    metering a predetermined amount of low pressure refrigerant from a refrigeration unit into an inflatable bag,
    sealing the refrigerant in the bag and allowing the refrigerant to equilibrate at ambient pressure whereby a homogeneous gas sample is formed within the bag,
    drawing a representative amount of the equilibrated sample through a contaminant tester tube to measure the amount of one or more selected contaminants in said representative sample.

2. The method of claim 1 that includes the further step of connecting a pump to the discharge end of the tester tube and selectively cycling the pump to draw a given volume of representative sample through the tester tube.

3. The method of claim 2 wherein about 100 cubic centimeters of representative sample is drawn through the tube tester.

4. The method of claim 1 wherein about 5 milliliters of refrigerant is metered into a bag that is expandable to hold about one liter of sample.

5. The method of claim 1 that includes the further steps of dividing the tester tube into a first section for detecting the amount of water present in sample and a second section for detecting the amount of acid present in said sample.

6. Apparatus for testing a low pressure refrigerant to detect the amount of contaminants in said refrigerant that includes,
    a gas tight inflatable bag having port means for allowing refrigerant to pass into and out of said bag,
    metering means for passing a given amount of refrigerant from a refrigeration unit into said bag,
    valve means associated with said port means for sealing the refrigerant within said bag whereby refrigerant sealed in said bag form a homogeneous sample at atmospheric pressure,
    a hollow contaminant tester tube having one end defining an entrance end the opposite end defining a discharge tube further including detection sections, each of which provides a visual indication of a selected contaminant contained in a refrigerant sample drawn through said tube,
    a connector means for coupling the entrance of said tube to the port means, and
    a pump means coupled to the discharge of said tube for drawing a representative sample of refrigerant from said bag through said tube when said valve means is opened.

7. The apparatus of claim 6 wherein said tube is formed of a transparent material and includes an oil removal zone adjacent the entrance end, and first and second contaminant detecting sections disposed in series downstream from said oil removal zone.

8. The apparatus of claim 7 wherein said first contaminant detecting section contains a material for determining the amount of water in a sample, and the second contaminant section contains a material for determining the amount of acid in said sample.

9. The apparatus of claim 6 wherein said inflatable bag is formed of a flaccid transparent material whereby the presence of a liquid in the bag can be visually perceived.

10. The apparatus of claim 6 wherein said pump is manually operated and is arranged to draw about 100 cubic centimeters of sample through said tube on each stroke of the pump.

11. The apparatus of claim 6 wherein the metering means contains means for coupling said metering means into a purge valve contained in the refrigeration unit.

12. The apparatus of claim 6 wherein said tester tube is enclosed within a protective housing.

* * * * *

UNITED STATES PATENT AND TRADEMARK OFFICE
CERTIFICATE OF CORRECTION

PATENT NO. : 4,803,843
DATED : 14 February 1989
INVENTOR(S) : Nancy M. Otto

It is certified that error appears in the above-identified patent and that said Letters Patent is hereby corrected as shown below:

TITLE PAGE: Column 1, INID Code [22], date of filing, change "Feb. 12, 1987" to -- Feb. 12, 1988 --.

Signed and Sealed this

Tenth Day of September, 1991

Attest:

HARRY F. MANBECK, JR.

*Attesting Officer*  *Commissioner of Patents and Trademarks*